United States Patent [19]
Liao et al.

[11] Patent Number: 6,036,891
[45] Date of Patent: Mar. 14, 2000

[54] POLYMERIZABLE HYDROPHILIC ULTRAVIOLET LIGHT ABSORBING MONOMERS

[75] Inventors: Xiugao Liao, Irvine; Ging-See Lee, Los Angeles; Stephen Q. Zhou, Ivine, all of Calif.

[73] Assignee: Pharmacia & Upjohn, Irvine, Calif.

[21] Appl. No.: 09/075,753

[22] Filed: May 11, 1998

[51] Int. Cl.$^7$ .............. F21V 9/06; C08L 39/04; C08K 5/3495; C07D 249/18; C08F 26/06; G03C 1/815

[52] U.S. Cl. .............. 252/588; 524/91; 524/916; 525/204; 526/261; 548/260; 548/261; 430/512

[58] Field of Search .............. 252/582, 588; 548/259, 260, 261; 524/91, 916; 526/261; 523/106; 430/512; 525/204

[56] References Cited

U.S. PATENT DOCUMENTS

| | | | |
|---|---|---|---|
| 4,528,311 | 7/1985 | Beard et al. | 524/91 |
| 4,611,061 | 9/1986 | Beard et al. | 548/260 |
| 4,716,234 | 12/1987 | Dunks et al. | 548/259 |
| 5,135,965 | 8/1992 | Tahan | 523/106 |
| 5,384,235 | 1/1995 | Chen et al. | 430/512 |

*Primary Examiner*—Shean C. Wu
*Attorney, Agent, or Firm*—Oppenheimer Wolff & Donnelly LLP

[57] ABSTRACT

Hydrophilic UV light absorbing polymerizing monomers are provided. These monomers are copolymerizable for providing biocompatible hydrogels capable of absorbing at least 90% of the UV light incident to the hydrogels. Such hydrogels are optically transparent, have high refractive indices, and possess long term stability. The hydrogels provided are useful in all applications where hydrogels may be used including intraocular lenses, corneal inlays, corneal onlays, contact lenses and similar applications.

27 Claims, 1 Drawing Sheet

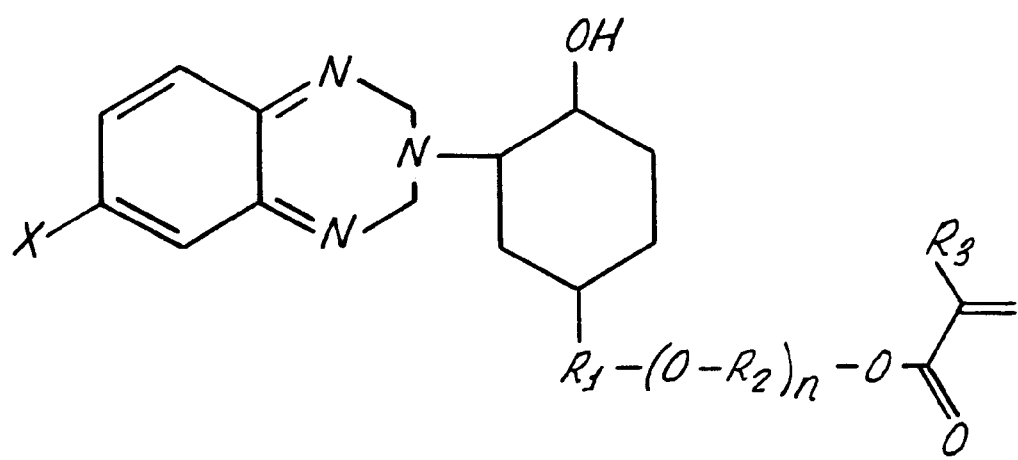

POLYMERIZABLE HYDROPHILIC ULTRAVIOLET LIGHT ABSORBING MONOMERS

BACKGROUND OF THE INVENTION

1. Field of the Invention

The present invention relates generally to hydrophilic ultraviolet light absorbing monomers. More particularly, this invention relates to ultraviolet light absorbing monomers polymerizable as co-monomers with other polymerizable monomers and co-polymers. In one of its more particular aspects, this invention relates to an ultraviolet light absorbing monomer polymerizable as a co-monomer with other suitable hydrophilic monomers into optically transparent, high refractive index hydrogels which are especially useful in the fabrication of intraocular lenses and contact lenses.

2. Description of Related Art

Optical devices in the form of intraocular lenses and contact lenses have been commercially available for several decades. For contact lenses, the primary indication for use has been as an adjunct for improving the wearer's visual acuity. This is accomplished by adding or subtracting small amounts of diopter power to the surface of the cornea. In addition, the contact lens also may have correction for astigmatism. A contact lens should be stable at temperatures at, or below, body temperature in an aqueous environment, non-toxic and not contain leachable compounds.

With intraocular lenses, the primary indication for use has been for the replacement of the natural crystalline lens of humans and other mammals that were lost to injury and/or cataract formation. The natural lens is generally a biconvex lens, from 6 to 13 mm in width, that has considerable optical power, nearly 20 diopters. Therefore, compared to a contact lens, replacing a damaged natural lens requires the use of a substantially larger, thicker, intraocular implant lens. Like the contact lens, an intraocular lens should be stable at body temperature in an aqueous environment, non-toxic and not contain leachable compounds.

Early on, the materials of choice for forming intraocular and contact lenses were the acrylates and methacrylates, particularly polymethylmethacrylate. These materials form rigid, glass-like lenses that are easily shaped to the desired optical correction. These compounds are successful as contact lenses and are generally known as the "hard" contact lenses.

These rigid, glassy polymers necessarily need to have diameters in the range of 6–13 mm to function as intraocluar lenses. Because these lenses are rigid, this limitation requires incisions into the eye of a correspondingly equal width. However, early surgical techniques to remove damaged lenses used large incisions, so the large size was not perceived as that great of a drawback. Such large incisions entail numerous complications and have protracted healing times. Advancements in the surgical technique for removing native lenses now provide for using smaller and smaller incisions, down in the 2–3 mm range. Consequently, the search was on to find suitable materials for use as an intraocular lens that could be inserted through smaller incisions.

To alleviate the drawbacks of using polyacrylates, such as polymethylmethacrylate, various hydrogels and elastomeric silicones have been developed that are rollable, foldable or deformable, yet resilient. When folded or deformed, the lens may be inserted into the eye through incisions as small as 2–3 mm. The resiliency of these materials provides for these lenses to re-assume their original biconvex optical shape after insertion. The materials used in these soft lenses have proven to provide optically clear lenses with sufficient indices of refraction, yet are strong or resilient enough to withstand the folding, deformation or rolling processes needed to achieve the smaller incision sizes. The folding, deforming or rolling capabilities of these substances, providing for smaller incisions, is a substantial improvement for the patient in terms of reduced trauma to the eye, improved post surgical healing and reduction in complications.

Softness and resilience is not the only improvement that has been sought. Another improvement being sought is ultraviolet (UV) light protection. As research into UV light exposure progresses, our understanding of the numerous deleterious effects of UV light exposure is growing. More and more products are being developed each year to decrease or prevent exposure to the harmful effects of UV light. UV light absorption for contact and intraocular lenses is at least as important as UV absorption for skin found in sun screens. What amount of UV light protection a native lens provides is lost when it is removed, increasing the risk to the retina from deleterious exposure to UV light if that protection is not restored. UV light protection for the eye may be enhanced by providing UV absorbers in contact lenses or in intraocular lens implants.

The use of UV light absorbers in hydrogels for use in contact and intraocular lenses poses other problems, as well. Optical hydrogels suitable for use in contact or intraocular lenses need clarity, good optical power, stability and resilience. Because of the long term use of contact and intraocular lenses, especially for intraocular lenses, the UV light absorbing compound should stay put within the copolymer. If the UV light absorber leaches out, there is the risk to the surrounding tissue from the chemical exposure. There is also the increasing risk from UV exposure as the UV light absorption capability diminishes over time.

UV light absorbers for use in hydrogels should be polymerizable as a comonomer in the hydrogel. Benzophenone based UV absorbers are polymerizable, but the resultant polymers may not be thermally stable, particularly when hydrated. The UV absorbing portion cleaves and leaches out of the polymer.

In addition, these UV absorbers are hydrophobic and not very soluble with hydrophilic hydrogel comonomers and copolymers. Even though these compounds are somewhat soluble with hydrophilic comonomers and copolymers, when hydrated within a hydrogel, they tend to coalesce from microphase separation. This coalescence clouds the material rendering it undesirable for use as a lens.

Another general class of UV light absorber is the class of phenylbenzotriazoles, such as 2-(2'-hydroxy-5'-methacryloxyethylphenyl)-2H-benzotriazole and its derivatives. These derivatives are polymerizable and stable against hydrolysis, and like the phenol based UV light absorbers, these compounds tend to be hydrophobic. The hydrophobic characteristic leads to microphase separation and clouding.

The hydrophobicity of the UV light absorber also decreases the amount of water absorption into the hydrogel. The decreased water absorption creates a harder, less resilient hydrogel material. To counter these drawbacks, the amount of UV light absorber is kept to a minimum to make a resilient, optically clear hydrogel. As a consequence, current use of hydrophobic UV light absorbers in optically clear material do not produce hydrogels with substantial UV light absorbing characteristics. In today's regulatory environment, substantial UV light absorption is at least 90% absorption of light at or below 372 nm wavelength.

It is, therefore, an object of the present invention to provide stable, polymerizable UV light absorbing monomers having increased hydrophilicity.

Another object of the present invention is to provide stable increased hydrophilicity UV light absorbing hydrogels having the properties of optical transparency and resiliency while substantially absorbing UV light.

Other objects and advantages of the present invention will become apparent from the following disclosure and description.

SUMMARY OF THE INVENTION

The present invention accomplishes the above-mentioned objectives and others by providing novel hydrophilic polymerizable UV light absorbing compositions suitable for copolymerization with other comonomers and copolymers. The copolymers of the present invention, upon cross-linking and hydration, provide for hydrogels having high optical clarity, high water content, high index of refraction, are stable with good resiliency, and absorb at least 90% of the incident UV light at wavelengths at or below 400 nm. In the present context, optical clarity shall refer to above 90% light transmission for wavelengths in the visual spectrum. The hydrogels are non-toxic and suitable for implantation within living systems. In particular, these hydrogels are suitable for use as UV light absorbing contact and intraocular lenses.

The novel hydrophilic UV light absorbing compositions comprise 2-(2'-hydroxy-5'-acryloxyalkoxyalkylphenyl)-2H-benzotriazoles. These novel hydrophilic UV light absorbing compositions are exemplified by 2-(2'-hydroxy-5'-methacryloxyethyoxymethylphenyl)-2H-benzotriazole. The ethylene oxide group may also be a linear repeating unit, repeating for up to ten ethylene oxide groups.

The benzotriazole based UV absorbers, like other UV light absorbing compositions, are generally hydrophobic and are not soluble in water. The ethylene oxide repeating units are the source of the hydrophilic character of the novel compositions of the present invention. By adjusting the number of repeating units of ethylene oxide, along with the number of repeating hydrophobic methylene groups, the hydrophilicity of these novel UV light absorbers can be adjusted for different applications.

The exemplary compound, 2-(2'-hydroxy-5'-methacryloxyethyoxymethylphenyl)-2H-benzotriazole, may be synthesized using the corresponding 2-(2'-hydroxy-5'-hydroxyalkoxyalkylphenyl)-2H-benzotriazole reacting with methacryloyl chloride in the presence of pyridine in co-solvents of ethyl ether and dichloromethane at 0–10° C.

The choices for other comonomers for use in the hydrogels of the present invention may either be derivatives of acrylic acid, such as acrylates, methacrylates, acrylamides or methacrylamides; vinyl-substituted amides; or nitrogen-containing heterocyclic compounds which are substituted with unsaturated sidechains, such as vinyl or acryloyl sidechains.

Hydrogel materials of the present invention include copolymers formed of at least one hydrophilic or water soluble monomer. Other, additional comonomers may be hydrophobic or hydrophilic. Particular examples are copolymers of various acrylate and acrylamide compounds such as 2-hydroxyethyl methacrylate, N,N-dimethylacrylamide, and N-benzyl-N-methylacrylamide, along with a cross-linking compound such as ethylene glycol dimethacrylate. These compounds are allowed to undergo sufficient cross-linking to hydrate to hydrated equilibrium water contents ranging from about 15% to about 65% and have refractive indices, $n_D^{20}$, ranging from 1.41 to 1.52, wet. The comonomers are polymerized with from about 1% to about 5% of the hydrophilic polymerizable UV light absorbing comonomers of the present invention, resulting in stable, non-toxic, hydrogels that also exhibit UV light absorption of at least 90% of light at or below 400 nm wavelength. These optically clear UV light absorbing hydrogels are useful in intraocular lenses, contact lenses and related applications.

BRIEF DESCRIPTION OF THE DRAWING

The FIGURE depicts a general formula for the exemplary compositions, 2-(2'-hydroxy-5'-acryloxy(alkoxy)$_n$alkylphenyl)-2H-benzotriazole, of the present invention, where X=hydrogen or a halogen, n=1–10, and R=hydrogen or a methyl group.

DETAILED DESCRIPTION OF THE EXEMPLARY EMBODIMENTS

The present invention provides novel hydrophilic UV light absorbing polymerizable compositions which provide further for hydrophilic UV light absorbing polymeric materials which are suitable for forming hydrogels. The UV light absorbing compositions within the hydrogels are hydrolytically stable and non-leachable. Hydrogels of the present invention are optically clear UV light absorbing cross-linked polymers and copolymers. Hydrogels, generally, and processes for their formation are well documented in the literature.

An exemplary class of UV light absorbing hydrogel-forming polymers includes cross-linked polymers and copolymers which hydrate to a relatively high hydrated equilibrium water content. As pointed out above, however, high water content UV light absorbing hydrogels generally have difficulty with microphase separation of the hydrophobic UV light absorbers which dramatically interfere with the optical clarity of the hydrogel. Decreasing the content of hydrophobic UV light absorber may solve the microphase problem, only to substantially decrease the efficacy of the UV light absorption characteristic. The hydrogel polymers and copolymers of the present invention have water equilibrium contents of 15% or greater. The hydrogel polymers of the present invention have refractive indices of at least 1.41. The hydrogel polymers of the present invention have sufficient content of hydrophilic UV light absorbers to provide at least 90% absorption of incident UV light at or below 400 nm wavelength without appreciable loss of optical clarity.

Referring to FIG. 1, the present invention provides novel hydrophilic polymerizable UV light absorbing compositions having the general formula 2-(2'-hydroxy- 5'-acryloxy(alkyloxy)$_n$alkylphenyl)-2H-benzotriazole. The alky portion of the compositions are methylene or repeating units of methylene and is hydrophobic. The alkyloxy portion of the compound, represented by "n" in the formula, is alkylene oxide or repeating units of alkylene oxide, such as ethylene oxide or propylene oxide, and is hydrophilic. The coexistence of the hydrophobic methylene repeating units with the hydrophilic alkylene oxide repeating units is part of the unique character of this novel class of UV light absorbers.

The degree of hydrophilicity of this class of UV light absorbers can be adjusted by manipulating the number of repeating methylene and alkylene oxide repeating units. This manipulation provides for tailoring of the compound to achieve a desirable range of hydrophilicity for use in different applications. Exemplary compounds of the present invention include 2-(2'-hydroxy-5'- methacryloxyethoxymethylphenyl)-2H-benzotriazole and 2-(2'-hydroxy-5'-methacryloxyethoxyethylphenyl)-2H-benzotriazole.

The exemplary 2-(2'-hydroxy-5'-acryloxy(alkoxy)$_n$alkylphenyl)-2H-benzotriazoles can be synthesized from 2-(2'-hydroxy-5'-hydroxy(alkoxy)$_n$alkylphenyl-2H-benzotriazole by reaction with methacryloyl chloride in the presence of pyridine in co-solvents of ethyl ether and dichloromethane at 0–10° C. 2-(2'-hydroxy-5'-acryloxy(alkoxy)$_n$alkylphenyl)-2H-benzotriazole is polymerizable as a comonomer with a wide variety of comonomers to form polymers and copolymers.

With cross-linking and hydration, the exemplary hydrophilic comonomers yield hydrogels having high water content, high refractive index $n_D^{20}/n_D^{37}$, and good strength, resiliency and stability. When used in an amount of about 1 weight percent to about 5 weight percent in the hydrogel, 2-(2'-hydroxy-4'-acryloxy(alkoxy)$_n$alkylphenyl-2H-benzotriazole provides the hydrogels with a UV light absorption of at least 90% absorption of light at or below 400 nm wavelengths.

Many of the monomers and polymers currently utilized to form hydrogels are suitable for forming the UV light absorbing hydrogels of the present invention. Generally, hydrogel forming polymers are cross-linked polymers of water soluble or hydrophilic monomers or copolymers of water soluble and water insoluble monomers. Exemplary comonomers which can be used in the present invention include:

| | |
|---|---|
| alkyl acrylates (alkyl = 1–6 carbon) | 3-(N,N-dimethylamino) propylacrylamide |
| phenyl acrylate | allylacrylamide |
| hydroxyethyl acrylate | hydroxymethyldiacetoneacrylamide |
| hydroxypropyl acrylate | N,N-dimethylacrylamide |
| hydroxybutyl acrylate | N,N-diethylacrylamide |
| glycerol monoacrylate | N-ethyl-N-methylacrylamide |
| 2-phenoxyethyl acrylate | N-methylmethacrylamide |
| 2-N-morpholinoethyl acrylate | N-methylolmethacrylamide |
| 2-(2-ethoxyethoxy)ethyl acrylate | N-(2-hydroxypropyl) methacrylamide |
| 2-(N,N-dimethylamino)ethyl acrylate | N-4-(hydroxyphenyl) methacrylamide |
| 3-(N,N-dimethylamino)propyl acrylate | N-(3-picolyl)methacrylamide |
| alkyl methacrylates (alkyl - 1–6 carbon) | 3-vinylpyridine |
| furfuryl methacrylate | 4-vinylpyridine |
| hydroxyethyl methacrylate | N-vinylpyrrolidinone |
| hydroxypropyl methacrylate | vinyl pyrazine |
| hydroxybutyl methacrylate | 2-methyl-5-vinylpyrazine |
| glycerol monomethacrylate | 4-vinylpyrimidine |
| 2-phenoxyethyl methacrylate | vinyl pyridazine |
| 2-N-morpholinoethyl methacrylate | N-vinylimidazole |
| 2-(N,N-dimethylamino)ethyl methacrylate | N-vinylcarbazole |
| 3-(N,N-dimethylamino)propyl methacrylate | N-vinylsuccinimide |
| 2-pyrrolidinonylethyl methacrylate | 4-methyl-5-vinylthiazole |
| N-alkyl acrylamides (alkyl = 1–8 carbon) | N-acryloylmorpholine |
| N-(n-octadecylacrylamide) | N-methyl-N-vinylacetamide |

Exemplary cross-linking agents which can be used to produce the hydrogels of the present invention include 1,3-propanediol diacrylate, 1,4-butanediol diacrylate, 1,6-hexamethylene diacrylate, 1,4-phenylene diacrylate, glycerol tris (acryloxypropyl), ether, ethylene glycol dimethacrylate, 1,3-propanediol dimethacrylate, 1,6-hexamethylene dimethacrylate, 1,10-decanediol dimethacrylate, 1,12-dodecanediol dimethacrylate, triethylene glycol dimethacrylate, glycerol trimethacrylate, N,N'-octamethylenebisacrylamide, N,N'-dodecanomethylenebisacrylamide, N,N'-(1,2-dihydroxyethylene)bisacrylamide, allyl methacrylamide, divinylpyridine, 4,6-divinylpyrimidine, 2,5-divinylpyrazine, 1,4-divinylimidazole, 1,5-divinylimidazole, and divinylbenzene. The cross-linking agents may be used in amounts of about 0.01 weight percent to 1.0 weight percent.

The relative amounts of the various comonomers and other reagents used to produce the hydrogel materials will depend upon the desired strengths, final water contents, refractive indicies, and elasticities needed in order to apply the hydrogels to a specific application. Hydrogels prepared using the exemplary 2-(2'-hydroxy-5'-acryloxy(alkoxy)$_n$alkylphenyl-2H-benzotriazoles of the present invention have the properties desired for use in a wide variety of applications for UV absorption in hydrogels that require high UV absorption, strength, hydrophilicity and long term stability.

In accordance with the present invention, an exemplary UV light absorbing hydrogel copolymer is 2-hydroxyethyl methacrylate polymerized with N,N-dimethylacrylamide and 2-(2'-hydroxy-5'-methacryloxyethoxymethylphenyl)-2H-benzotriazole cross-linked with ethylene glycol dimethacrylate. An additional exemplary hydrogel copolymer is 2-hydroxyethyl methacrylate polymerized with N,N-dimethylacrylamide and 2-(2'-hydroxy-5'-methacryloxyethoxyethylphenyl)-2H-benzotriazole cross-linked with ethylene glycol dimethacrylate.

The following examples are offered as being illustrative of the principles of the present invention and not by way of limitation.

EXAMPLE 1

Synthesis of 2-(2'-hydroxy-5'-methacryloxyethoxymethylphenyl)-2H-benzotriazole

A quantity of 180 ml of methylene chloride was poured into a three necked flask containing 30 g of 2-(2'-hydroxy-5'-hydroxyethoxymethylphenyl)-2H-benzotriazole and stirred until starting chemicals were dissolved. To this reaction system 13.5 g of pyridine and 120 ml of anhydrous ethyl ether were sequentially added. 15.3 g of methacryloyl chloride in 60 ml of anhydrous ethyl ether were placed in an addition funnel. The reaction vessel was cooled over ice water to 0–10°. The solution from the addition funnel was dropped, with stirring, into the reaction mixture over 45 minutes. Stirring was continued at this temperature for 2–3 hours.

After warming the reaction mixture to room temperature, stirring was continued for 12–24 hours. The solid salt was removed with filtration and the liquid solution transferred into a separatory funnel. This solution was washed with 150 ml of 2N HCl solution. If the separation was not clear, 150 ml of water was added. The water layer was extracted with 150 ml of methylene chloride and the organic layer combined. The organic layer was washed with 150 ml of saturated sodium bicarbonate solution and then dried with magnesium sulfate. The solvent was then removed.

The residue was dissolved into 150 ml of ethanol and then cooled in a freezer to −20 to −45° C. for 12 to 24 hours to form a precipitate. The white powdery precipitate was filtered quickly under low temperature and dried under vacuum at room temperature. Under ultrasound, the dried powder was dissolved into 150 ml of a mixture of ethanol and methanol (3:2) and filtered to remove remaining impurities yielding approximately 20 g of 2-(2'-hydroxy-5'-methacryloxyethoxymethylphenyl)-2H-benzotriazole.

EXAMPLE 2

Synthesis of 2-(2'-hydroxy-5'-methacryloxyethoxyethylphenyl)-2H-benzotriazole

The procedure of Example 1 was repeated using instead 2-(2'-hydroxy-5'-hydroxyethoxyethylphenyl)-2H-benzotriazole as the starting material as follows. A quantity of 180 ml of methylene chloride was poured into a three necked flask containing 30 g of 2-(2'-hydroxy-5'-hydroxyethoxyethylphenyl)-2H-benzotriazole and stirred until starting chemicals were dissolved. To this reaction system 13.5 g of pyridine and 120 ml of anhydrous ethyl ether were sequentially added. 15.3 g of methacryloyl chloride in 60 ml of anhydrous ethyl ether were placed in an addition funnel. The reaction vessel was cooled over ice water to 0–10°. The solution from the addition funnel was dropped, with stirring, into the reaction mixture over 45 minutes. Stirring was continued at this temperature for 2–3 hours.

After warming the reaction mixture to room temperature, stirring was continued for 12–24 hours. The solid salt was removed with filtration and the liquid solution transferred into a separatory funnel. This solution was washed with 150 ml of 2N HCl solution. If the separation was not clear, 150 ml of water was added. The water layer was extracted with 150 ml of methylene chloride and the organic layer combined. The organic layer was washed with 150 ml of saturated sodium bicarbonate solution and then dried with magnesium sulfate. The solvent was then removed.

The residue was dissolved into 150 ml of ethanol and then cooled in a freezer to –20 to –45° C. for 12 to 24 hours to form a precipitate. The white powdery precipitate was filtered quickly under low temperature and dried under vacuum at room temperature. Under ultrasound, the dried powder was dissolved into 150 ml of a mixture of ethanol and methanol (3:2) and filtered to remove remaining impurities yielding approximately 20 g of 2-(2'-hydroxy-5'-methacryloxyethoxyethylphenyl)-2H-benzotriazole.

The following example illustrates the polymerization of 2-(2'-hydroxy-5'-acryloxy(alkoxy)$_n$alkylphenyl-2H-benzotriazoles and various other monomers.

which was pretreated with a trimethylchlorosilane mold releasing agent. Each ampule was then attached to a vacuum system and cooled with liquid nitrogen. After the mixture was frozen, the mixture was placed under vacuum. When a constant pressure was achieved, the vacuum was turned off and the mixture was allowed to thaw, assisted by warming in a water bath. This freeze-thaw cycle was repeated two to four times in order to provide sufficient degassing of the mixture. Finally, each mixture was sealed in the ampule under vacuum or an inert gas, such as nitrogen or argon, and polymerized at a temperature of 60° C. for a period of 24 hours, then at 135° C. for 10 hours.

After the polymerized materials were cooled, each ampule was broken open and the resulting polymer rods were cut into blanks. Each blank was then machined to an intraocular lens in its dehydrated state. The machined dehydrated lenses had diameters ranging from approximately 6 to 13 mm and central lens thicknesses ranging from approximately 0.5 to 2.0 mm.

Each lens was immersed in physiologically buffered aqueous solution for 8 to 48 hours and allowed to hydrate to its equilibrium water content. The lenses were observed to expand slightly while retaining their original conformations.

TABLE I

| COMPONENT | ABBREVIATION |
|---|---|
| 2-hydroxyethyl methacrylate | HEMA |
| N,N-dimethylacrylamide | DMA |
| N-benzyl-N-methylacrylamide | BMA |
| 2-(2'-hydroxy-5'-methacryloxyethyloxymethylphenyl)-2H-benzotriazole | HMMB |
| 2-(2'-hydroxy-5'-methacryloxyethyloxyethylphenyl)-2H-benzotriazole | HMEB |
| ethylene glycol dimethacrylate | EGDMA |
| 2,2'-azobisisobutyronitrile | AIBN |
| dicumyl peroxide | DCP |

TABLE II

|   | HEMA | DMA | BMA | HMMB | HMEB | EGDMA | AIBN | DCP |
|---|---|---|---|---|---|---|---|---|
| 1 | 60% | 15% | 25% | 1.0% |  | 1.0% | 0.02% | 0.02% |
| 2 | 71% | 5% | 24% | 1.0% |  | 0.6% | 0.02% | 0.02% |
| 3 | 71% | 5% | 24% | 2.0% |  | 0.6% | 0.02% | 0.02% |
| 4 | 71% | 5% | 24% |  | 2.0% | 0.6% | 0.02% | 0.02% |

EXAMPLE 3

A total of four different copolymers were prepared and evaluated for use as exemplary hydrogel forming materials. Abbreviations for the various compositions used are given in the immediately following Table I. Table II subsequently illustrates the proportions of each component of the polymerization mixture and the cross-linker used. The properties of the copolymers are illustrated in Table III immediately thereafter. The amount of water absorbed by the hydrogels is dependent on the degree of cross-linking allowed.

Each polymerization procedure was carried out by first mixing the appropriate amounts of the monomers and cross-linkers with 2,2'-azobisisobutyronitrile as a polymerization initiator. Then each mixture was transferred to an ampule For each lens so produced the refractive indicies, Shore A hardness, UV absorption, and toxicity were determined using appropriate ANSI protocols as known in the art. Water contents were measured by taking the difference in weight between each hydrated lens versus the respective dry hydrogel lens weight and then dividing by the appropriate hydrated weight to determine the water content percentage of each lens. Lens optical clarity was measured by suspending each hydrated lens in aqueous solution and then measuring the percentage transmission of the incident light of a 632 nm laser passing through the lens. The results were tabulated in Table III.

TABLE III

| | RI (wet) | Clarity | Water (%) | Hardness | UV (abs) | Toxicity |
|---|---|---|---|---|---|---|
| 1 | 1.4754 | Clear | 20.3% | 29 | 381.1 nm | Non-toxic |
| 2 | 1.4877 | Clear | 21.6% | 26 | 382.5 nm | Non-toxic |
| 3 | 1.4890 | Clear | 21.0% | 25 | 386.4 nm | Non-toxic |
| 4 | 1.4879 | Clear | 21.8% | 30 | 390.5 nm | Non-toxic |

The hydrophilic UV light absorbing monomers of the present invention provide for the creation of UV light absorbing polymers, copolymers and hydrogels. These products are useful in a large number applications under a number of different circumstances. The hydrophilic UV light absorbing monomers balance the hydrophobic moieties of the compositions with a hydrophilic moiety while providing for substantial UV light absorption, at least 90%, without loss of optical clarity. For applications using hydrogels with higher water content, a higher number of alkylene oxide groups, with fewer methylene groups, are used in the UV light absorbers of the present invention. The desired optical clarity was achieved through balancing the presence of the hydrophilic moiety necessary to keep the UV light absorber hydrated at higher concentrations of UV light absorber and/or higher water contents against the need to keep the UV light absorber from undergoing appreciable microphase separation.

Having thus described exemplary embodiments of the present invention, it should be noted by those skilled in the art that the disclosures herein are exemplary only and that alternatives, adaptations and modifications may be made within the scope of the present invention.

What is claimed is:

1. A monomer having the general formula:

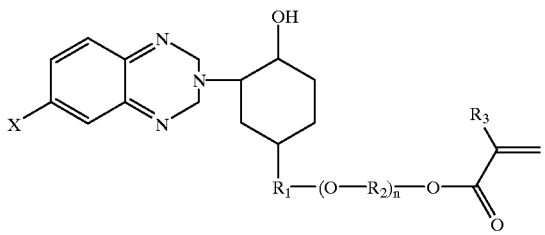

wherein:

X is hydrogen or a halogen;

$n$ is a number from 1 to 10;

$R_1$ is a non-branching alkyl group having from 1–6 carbon atoms;

$R_2$ is 1 to 5 alkyl groups; and $R_3$ is hydrogen or methyl group.

2. A homopolymer comprising a polymerized monomer having the formula:

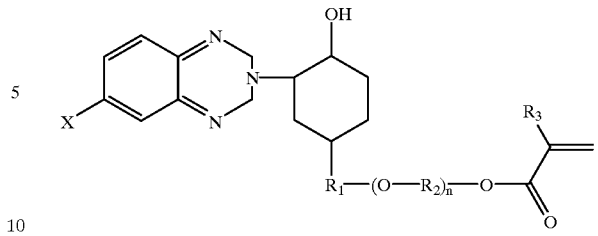

wherein:

X is hydrogen or a halogen;

$n$ is a number from 1 to 10;

$R_1$ is a non-branching alkyl group having from 1–6 carbon atoms;

$R_2$ is 1 to 10 alkyl groups; and $R_3$ is hydrogen or methyl group.

3. A hydrogel comprising a cross-linked copolymer comprising one comonomer having the formula:

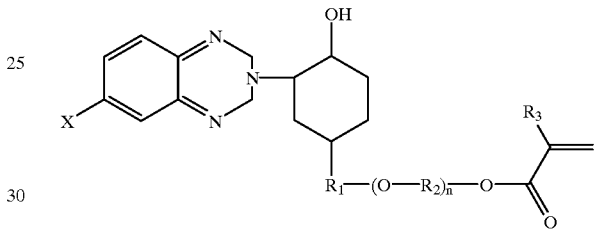

wherein:

X is hydrogen or a halogen;

$n$ is a number from 1 to 10;

$R_1$ is a non-branching alkyl group having from 1–6 carbon atoms;

$R_2$ is 1 to 5 alkyl groups; and $R_3$ is hydrogen or methyl group;

and at least one polymerizable comonomer.

4. The hydrogel of claim 3 wherein said at least one polymerizable comonomer is selected from the group consisting of acrylates, methacrylates, acrylamides, methacrylamides, vinyl-substituted amides, vinyl-substituted nitrogen-containing heterocyclic compounds, and acryloyl-substituted nitrogen-containing heterocyclic compounds.

5. The hydrogel of claim 3 wherein said at least one polymerizable comonomer is selected from the group consisting of methyl acrylate, ethyl acrylate, propyl acrylate, butyl acrylate, amyl acrylate, hexyl acrylate, phenyl acrylate, hydroxyethyl, acrylate, hydroxypropyl acrylate, hydroxybutyl acrylate, glycerol monoacrylate, 2-phenoxyethyl acrylate, 2-N-morpholinoethyl acrylate, 2-(2-ethoxyethoxy)ethyl acrylate, 2-(N,N-dimethylamino) ethyl acrylate, 3-(N,N-dimethylamino)propyl acrylate, methyl methacrylate, ethyl methacrylate, propyl methacrylate, butyl methacrylate, amyl methacrylate, hexyl methacrylate, furfuryl methacrylate, hydroxyethyl methacrylate, hydroxypropyl methacrylate, hydroxybutyl methacrylate, glycerol monomethacrylate, 2-phenoxyethyl methacrylate, 2-N-morpholinoethyl methacrylate, 2-(N,N-dimethylamino)ethyl methacrylate, 3-(N,N-dimethylamino) propyl methacrylate, 2-pyrrolidinonylethyl methacrylate, N-methylacrylamide, N-ethylacrylamide, N-propylacrylamide, N-butylacrylamide, N-amylacrylamide, N-hexylacrylamide, N-heptylacrylamide, N-octylacrylamide, N-(n-octadecylacrylamide), 3-N,N-dimethylamino) propylacrylamide, allylacrylamide, hydroxymethyldiacetoneacrylamide, N,N-dimethylacrylamide, N,N-diethylacrylamide, N-ethyl-N-methylacrylamide, N-methylmethacrylamide, N-methylolmethacrylamide, N-(2-hydroxypropyl)methacrylamide, N-4-(hydroxyphenyl)methacrylamide, N-(30picolyl)methacrylamide, 3-vinylpyridine, 4-vinylpyridine, N-vinylpyrrolidinone, vinyl pyrzaine, 2-methyl-5-vinylpyrazine, 4-vinylpyrimidine, vinyl pyridazine, N-vinylimidazole, N-vinylcarbazole, N-vinylsuccinimide, 4-methyl-5-vinylthiazole, N-acryloylmorpholine, and N-methyl-N-vinylacetamide.

6. The hydrogel of claim 3 including a cross-linking agent selected from the group consisting of 1,3-propanediol diacrylate, 1,4-butanediol diacrylate, 1,6-hexamethylene diacrylate, 1,4-phenylene diacrylate, glycerol tris (acrylopxypropyl)ether, ethylene glycol dimethacrylate, 1,3-propanediol dimethacrylate, 1,6-hexamethylene dimethacrylate, 1,10-decanediol dimethacrylate, 1,12-dodecanediol dimethacrylate, triethylene glycol dimethacrylate, glycerol trimethacrylate, N,N'-octamethylenebisacrylamide, N,N'-dodecanomethylenebisacrylamide, N,N'-(1,2-dihydroxyethylene)bisacrylamide, allyl methacrylamide, divinylpyridine, 4,6-divinylpyrimidine, 2,5-divinylpyrazine, 1,4-divinylimidazole, 1,5-divinylimidazole, and divinylbenzene.

7. The hydrogel of claim 4 including a cross-linking agent selected from the group consisting of 1,3-propanediol diacrylate, 1,4-butanediol diacrylate, 1,6-hexamethylene diacrylate, 1,4-phenylene diacrylate, glycerol tris (acryloxypropyl)ether, ethylene glycol dimethacrylate, 1,3-propanediol dimethacrylate, 1,6-hexamethylene dimethacrylate, 1,10-decanediol dimethacrylate, 1,12-dodecanediol dimethacrylate, triethylene glycol dimethacrylate, glycerol trimethacrylate, N,N'-octamethylenebisacrylamide, N,N'-dodecanomethylenebisacrylamide, N,N'-(1,2-dihydroxyethylene)bisacrylamide, allyl methacrylamide, divinylpyridine, 4,6-divinylpyrimidine, 2,5-divinylpyrazine, 1,4-divinylimidazole, 1,5-divinylimidazole, and divinylbenzene.

8. An intraocular lens fabricated from the homopolymer of claim 2.

9. An intraocular lens fabricated from the hydrogel of claim 3.

10. An intraocular lens fabricated from the hydrogel of claim 4.

11. An intraocular lens fabricated from the hydrogel of claim 5.

12. An intraocular lens fabricated from the hydrogel of claim 6.

13. An intraocular lens fabricated from the hydrogel of claim 7.

14. The hydrogel of claim 3 having a refractive index, $n_D^{37}$, of 1.41 to 1.52 in the fully hydrated state.

15. The hydrogel of claim 3 having an equilibrium water content of 15% to 65%.

16. The hydrogel of claim 3 wherein the hydrogel includes about 1 weight % to about 5 weight % of the comonomer 2-(2'-hydroxy-5'-methacryloxyalkoxyalkylphenyl)-2H-benzotriazole.

17. The hydrogel of claim 3 including an effective amount of 2-(2'-hydroxy-5'-methacryloxyalkoxyalkylphenyl)-2H-benzotriazole to provide a UV light absorption of at least 90% of the UV light incident to the hydrogel.

18. A composition of matter having the formula 2-(2'-hydroxy-5'-methacryloxyethoxymethylphenyl)-2H-benzotriazole.

19. A composition of matter having the formula 2-(2'-hydroxy-5'-methacryloxyethoxyethylphenyl)-2H-benzotriazole.

20. A hydrogel comprising a cross-linked copolymer prepared from a mixture of comonomers including 2-(2'-hydroxy-5'-methacryloxyethoxymethylphenyl)-2H-benzotriazole and at least one polymerizable comonomer.

21. A hydrogel comprising a cross-linked copolymer prepared from a mixture of comonomers including 2-(2'-hydroxy-5'-methacryloxyethoxyethylphenyl)-2H-benzotriazole and at least one polymerizable comonomer.

22. An optically clear hydrogel comprising a monomer having the general formula:

wherein:

X is hydrogen or a halogen;

$n$ is a number from 1 to 10;

$R_1$ is a non-branching alkyl group having from 1–6 carbon atoms;

$R_2$ is 1 to 5 alkyl groups; and $R_3$ is hydrogen or methyl group.

23. The optically clear hydrogel of claim 22 having an equilibrium water content of at least 15 weight %.

24. The optically clear hydrogel of claim 23 having an index of refraction, $n_D^{37}$, of at least 1.41.

25. The optically clear hydrogel of claim 20 including 2-(2'-hydroxy-5'-methacryloxyethoxyethylphenyl)-2H-benzotriazole.

26. The optically clear hydrogel of claim 22 including 2-(2'-hydroxy-5'-methacryloxyethopymethylphenyl)-2H-benzotriazole.

27. The optically clear hydrogel of claim 22 having an ultraviolet light transmission of 10% or less at wavelengths at or below 400 nanometers.

* * * * *